(12) United States Patent
Himeno (10) Patent No.: US 12,067,350 B2
(45) Date of Patent: Aug. 20, 2024

(54) DOCUMENT CREATION SYSTEM

(71) Applicant: IRYOU JYOUHOU GIJYUTU KENKYUSHO CORPORATION, Fukuoka (JP)

(72) Inventor: Shinkichi Himeno, Fukuoka (JP)

(73) Assignee: IRYOU JYOUHOU GIJYUTU KENKYUSHO CORPORATION, Fukuoka (JP)

( * ) Notice: Subject to any disclaimer, the term of this patent is extended or adjusted under 35 U.S.C. 154(b) by 166 days.

(21) Appl. No.: 17/672,336

(22) Filed: Feb. 15, 2022

(65) Prior Publication Data

US 2022/0180047 A1 Jun. 9, 2022

Related U.S. Application Data

(63) Continuation-in-part of application No. PCT/JP2020/040029, filed on Oct. 26, 2020.

(30) Foreign Application Priority Data

Nov. 2, 2019 (JP) .................. 2019-200337

(51) Int. Cl.
*G06F 40/166* (2020.01)
*G06F 40/117* (2020.01)
*G16H 10/60* (2018.01)

(52) U.S. Cl.
CPC .......... *G06F 40/166* (2020.01); *G06F 40/117* (2020.01); *G16H 10/60* (2018.01)

(58) Field of Classification Search
CPC ...... G06F 40/166; G06F 40/117; G16H 10/60
See application file for complete search history.

(56) References Cited

U.S. PATENT DOCUMENTS

| | | | | |
|---|---|---|---|---|
| 6,468,210 B2 * | 10/2002 | Iliff | ......... | G16H 50/20 706/45 |
| 6,475,143 B2 * | 11/2002 | Iliff | ......... | G16H 15/00 128/920 |
| 7,043,437 B1 * | 5/2006 | Nielsen | ......... | G16H 10/60 704/7 |
| 7,165,062 B2 * | 1/2007 | O'Rourke | ......... | G16H 10/60 707/999.005 |

(Continued)

FOREIGN PATENT DOCUMENTS

| | | |
|---|---|---|
| JP | 2004-326626 A | 11/2004 |
| JP | 3176303 U | 6/2012 |

(Continued)

OTHER PUBLICATIONS

Safran C. Update on Data Reuse in Health Care. Yearb Med Inform. Aug. 2017;26(1):24-27. doi: 10.15265/IY-2017-013. Epub Sep. 11, 2017. PMID: 29063535; PMCID: PMC6239227. (Year: 2017).*

(Continued)

*Primary Examiner* — Benjamin Smith
(74) *Attorney, Agent, or Firm* — Maier & Maier, PLLC (57) ABSTRACT

A document creation system for creating documents corresponding to each case and falling into multiple document categories includes an input item tag creation configured to create input item tags, an input item tag list management configured to manage a list of the input item tags, and a tag-attached document creation configured to create a document using the input item tags.

6 Claims, 5 Drawing Sheets

(56) References Cited

U.S. PATENT DOCUMENTS

| | | | |
|---|---|---|---|
| 7,225,408 B2* | 5/2007 | O'Rourke | G06F 21/6254 715/744 |
| 7,802,183 B1* | 9/2010 | Essin | G16H 10/60 715/255 |
| 8,069,411 B2* | 11/2011 | Titemore | G06F 40/237 715/255 |
| 8,086,468 B2* | 12/2011 | Kim | G16H 70/20 705/2 |
| 9,569,838 B2* | 2/2017 | Enomoto | G16H 30/40 |
| 9,892,231 B2* | 2/2018 | Vdovjak | G16Z 99/00 |
| 9,971,848 B2* | 5/2018 | D'Souza | G06Q 10/10 |
| 10,249,386 B2* | 4/2019 | Blechman | G16H 10/60 |
| 10,319,466 B2* | 6/2019 | Lareau | G16H 10/60 |
| 10,657,613 B2* | 5/2020 | Bucur | G06Q 10/00 |
| 10,949,602 B2* | 3/2021 | Snider | G10L 15/26 |
| 11,024,424 B2* | 6/2021 | Sun | G16H 10/60 |
| 11,183,300 B2* | 11/2021 | Sadeghi | G06F 40/143 |
| 11,348,689 B1* | 5/2022 | Gonzales, Jr. | G06F 3/04817 |
| 11,568,996 B2* | 1/2023 | Li | G16H 50/50 |
| 2002/0002325 A1* | 1/2002 | Iliff | G16H 50/20 600/300 |
| 2002/0013515 A1* | 1/2002 | Iliff | G16H 15/00 128/923 |
| 2002/0068857 A1* | 6/2002 | Iliff | G16H 70/60 600/300 |
| 2002/0158911 A1* | 10/2002 | O'Rourke | G16H 10/60 715/810 |
| 2002/0161795 A1* | 10/2002 | O'Rourke | G16H 10/60 715/205 |
| 2007/0011608 A1* | 1/2007 | Titemore | G06F 16/93 715/209 |
| 2007/0088559 A1* | 4/2007 | Kim | G16H 40/20 715/705 |
| 2009/0204421 A1* | 8/2009 | Guimaraes | G16H 10/60 705/2 |
| 2011/0246237 A1* | 10/2011 | Vdovjak | G16H 10/60 705/3 |
| 2013/0080192 A1* | 3/2013 | Bucur | G06Q 10/00 705/3 |
| 2013/0231957 A1* | 9/2013 | Lareau | G16H 10/60 705/3 |
| 2014/0064563 A1* | 3/2014 | Enomoto | G06T 7/0012 382/103 |
| 2014/0365232 A1* | 12/2014 | Sadeghi | G16H 50/20 705/2 |
| 2014/0365239 A1* | 12/2014 | Sadeghi | G16H 50/20 705/3 |
| 2015/0213195 A1* | 7/2015 | Blechman | G16H 10/60 705/51 |
| 2015/0356198 A1* | 12/2015 | D'Souza | G16H 50/20 705/2 |
| 2016/0275245 A1* | 9/2016 | Sevenster | G16H 30/20 |
| 2016/0342670 A1* | 11/2016 | Smith | G16H 10/60 |
| 2017/0364639 A1* | 12/2017 | Vdovjak | G16H 10/60 |
| 2018/0081859 A1* | 3/2018 | Snider | G06F 40/44 |
| 2018/0278609 A1* | 9/2018 | Ando | H04L 67/306 |
| 2018/0373844 A1* | 12/2018 | Ferrandez-Escamez | G16H 50/20 |
| 2019/0130073 A1* | 5/2019 | Sun | G16H 10/60 |
| 2020/0211685 A1* | 7/2020 | Isernhagen | G16H 20/30 |
| 2020/0243177 A1* | 7/2020 | Terai | G16H 15/00 |
| 2021/0158907 A1* | 5/2021 | Sragow | G16H 10/60 |
| 2022/0093268 A1* | 3/2022 | Li | G16H 10/60 |
| 2022/0392630 A1* | 12/2022 | Horton | H04L 67/10 |
| 2023/0040999 A1* | 2/2023 | Webb | G16H 20/40 |
| 2023/0088474 A1* | 3/2023 | Sragow | G16H 10/60 705/2 |

FOREIGN PATENT DOCUMENTS

| | | | | |
|---|---|---|---|---|
| JP | 2013-065216 A | 4/2013 | | |
| JP | 6038376 B1 | 12/2016 | | |
| JP | 6585458 B2 | 10/2019 | | |
| WO | WO-2014146180 A1 * | 9/2014 | | G06F 19/3431 |

OTHER PUBLICATIONS

Weiskopf NG, Bakken S, Hripcsak G, Weng C. A Data Quality Assessment Guideline for Electronic Health Record Data Reuse. EGEMS (Wash DC). Sep. 4, 2017;5(1):14. doi: 10.5334/egems.218. PMID: 29881734; PMCID: PMC5983018. (Year: 2017).*

International Search Report mailed on Feb. 2, 2021, in corresponding to International Application No. PCT/JP2020/040029; 5 pages (with English Translation).

* cited by examiner

| INPUT ITEM TAG ID# | INPUT ITEM TAG | TAG-ATTACHED DOCUMENT REFERENCE LIST | | |
|---|---|---|---|---|
| 1 | CHIEF COMPLAINT | DOCTOR ARTICLE | | |
| 2 | SYMPTOMS | DOCTOR ARTICLE | | |
| 3 | FINDINGS | DOCTOR ARTICLE | | |
| 4 | DISEASE NAME | DOCTOR ARTICLE | NURSE ARTICLE | REHABILITATION ARTICLE |
| ⋮ | ⋮ | | | |
| 2001 | HEIGHT | NURSE ARTICLE | REHABILITATION ARTICLE | OPINION ON CARE |
| 2002 | WEIGHT | NURSE ARTICLE | REHABILITATION ARTICLE | OPINION ON CARE |
| 2003 | BLOOD PRESSURE | NURSE ARTICLE | REHABILITATION ARTICLE | OPINION ON CARE |
| ⋮ | ⋮ | | | |
| 2050 | SITTING-UP ON BED | NURSE ARTICLE | REHABILITATION ARTICLE | OPINION ON CARE |
| 2051 | GOING TO TOILET | NURSE ARTICLE | REHABILITATION ARTICLE | OPINION ON CARE |
| ⋮ | ⋮ | | | |
| 6001 | WALKING ABILITY | REHABILITATION ARTICLE | NURSE ARTICLE | OPINION ON CARE |
| 6002 | STAIR CLIMBING ABILITY | REHABILITATION ARTICLE | NURSE ARTICLE | OPINION ON CARE |
| ⋮ | ⋮ | | | |

| SCORE | CAREGIVER | ASSISTANCE | LEVEL OF ASSISTANCE |
|---|---|---|---|
| 7 | NOT REQUIRED | NOT REQUIRED | INDEPENDENT, ABLE TO DO ON THEIR OWN |
| 6 | NOT REQUIRED | NOT REQUIRED | TAKE TIME, REQUIRE APPARATUS OR SELF-HELP TOOL, MEDICATED, REQUIRE SAFETY CONSIDERATION, ABLE TO DO ON THEIR OWN |
| 5 | REQUIRED | NOT REQUIRED | REQUIRE MONITORING, PREPARATION, INSTRUCTION, AND/OR URGE, "PREPARATION" INCLUDE MOUNTING OF APPARATUS OR SELF-HELP TOOL, REQUIRE SOME MONITORING OR CAREGIVING |
| 4 | REQUIRED | REQUIRED | DO 75% OR MORE ON THEIR OWN, REQUIRE SOME MONITORING OR CAREGIVING |
| 3 | REQUIRED | REQUIRED | DO 50% OR MORE AND LESS THAN 75% ON THEIR OWN, REQUIRE SOME MONITORING OR CAREGIVING |
| 2 | REQUIRED | REQUIRED | DO 25% OR MORE AND LESS THAN 50% ON THEIR OWN, REQUIRE SOME MONITORING OR CAREGIVING |
| 1 | REQUIRED | REQUIRED | DO ONLY LESS THAN 25% ON THEIR OWN, REQUIRE SOME MONITORING OR CAREGIVING |

| | | | | |
|---|---|---|---|---|
| BLOOD PRESSURE : | 130/85 | 2019/11/5 | 11:35 | INOUE |
| | 145/90 | 2019/11/15 | 15:20 | YAMASHITA |
| | ⋮ | ⋮ | ⋮ | |

FIG. 7

DOCUMENT CREATION SYSTEM

TECHNICAL FIELD

The present invention relates to a document creation system that creates documents corresponding to each case and falling into multiple document categories, such as electronic medical records.

BACKGROUND

It is often necessary to create and manage documents corresponding to each case and falling into multiple document categories, such as the medical records of patients. In medical sites and the like, staff members in multiple job categories are required to create a wide variety of complicated record documents, such as patient observation records, test/treatment plans, and evaluations with respect to the executed plans. Skillfully creating such documents can be said to be the most important challenge in enhancing the efficiency of work.

Background art literature relating to the present application includes the following.

CITATION LIST

Patent Literature

Patent Literature 1: Japanese Patent No. 6038376
Patent Literature 2: Japanese Patent No. 6585458

SUMMARY

Searching for required information in a great number of documents in accordance with the situation requires many staff members to work for a long time. An omission or oversight during the search may result in even a medical accident. The reason for the omission or oversight is that the staff visually search for where the required information is recorded. The work of transcribing information such as the disease name or blood test data to a document having a different purpose and falling into a different document category also causes an increase in the amount of work.

The present invention has been made to solve the above background art problems, and an object thereof is to provide a document creation system that is efficient and prevents an oversight, for example, by avoiding confusion over tag attachment and facilitating detection of required information by attaching tags to input items forming a document (input item tags) and recording the same information in the same input item tag for centralized management, further facilitating detection of the required information by identifying the document category in which the required information lies, using a tag-attached document reference list between the input item tags and document categories, eliminating, when creating a new document using the input item tags, the work of manually transcribing information to the input item tags by automatically referring to information recorded in the same input item tags in an existing document, conversely performing a write to the same input item tags in an existing document in some cases so that information recorded in the same input item tags is updated or new information is added, and facilitating work in a document having a complicated structure by setting a higher-level input item tag in which multiple input item tags are organized.

As means for accomplishing the above object, a document creation system for creating documents corresponding to each case and falling into multiple document categories according to claim 1 includes (1) input item tag creation means configured to create input item tags, (2) input item tag list management means configured to manage a list of the input item tags, and (3) tag-attached document creation means configured to create a document using the input item tags.

According to the document creation system, the input item tag list management means includes tag-attached document reference list management means used when creating a tag-attached document using the input item tags and configured to manage a list of tag-attached documents referred to from the input item tags.

The document creation system includes document category-specific model document management means configured to register and manage a tag-attached document as a model of a document category.

According to the document creation system, the input item tags are objectized so as to include attributes thereof.

The document creation system includes input item tag reference means configured to, when creating the tag-attached document using the input item tags, search for an existing tag-attached document including input item tags identical to the input item tags and to copy the latest information described in the input item tags in the retrieved existing tag-attached document to the input item tags in the created tag-attached document.

The input item tag reference means includes latest time point setting means configured to set a time point in the past and to copy the latest information at the time point to the input item tags in the created tag-attached document.

According to the document creation system, when creating a tag-attached document using the input item tags, search for an existing tag-attached document including input item tags identical to the input item tags in the created tag-attached document and to write the latest information described in the newly created tag-attached document to the input item tags in the retrieved existing tag-attached document.

According to the document creation system, the input item tag write means includes write time/person additional write means configured to additionally write the time at which the information has been written and a person who has written the information.

According to the document creation system, the input item tag list management means includes higher-level input item tag setting means configured to set a higher-level input item tag in which multiple input item tags are organized, so that the input item tags can be referred to or written on the higher-level input item tag basis.

The document creation system includes the input item tag creation means and thus creates input item tags.

The document creation system includes the input item tag list management means and thus manages a list of the input item tags.

The document creation system includes the tag-attached document creation means and thus creates a document using the input item tags.

The document creation system of claim 2 includes the tag-attached document reference list management means and thus manages a list of tag-attached documents referred to from the input item tags.

The document creation system includes the document category-specific model document management means and thus registers and manages a tag-attached document as a model of a document category.

The document creation system has a function of objectizing the input item tags such that the objectized input item tags include attributes thereof.

The document creation system includes the input item tag reference means and thus searches for an existing tag-attached document including input item tags identical to the input item tags in the created tag-attached document and copies the latest information described in the input item tags in the retrieved existing tag-attached document to the input item tags in the created tag-attached document.

The document creation system includes the latest time point setting means and thus sets a time point in the past and copies the latest information at the time point to the input item tags in the created tag-attached document.

The document creation system includes the input item tag write means and thus searches for an existing tag-attached document including input item tags identical to the input item tags in the created tag-attached document and writes the latest information described in the newly created tag-attached document to the input item tags in the retrieved existing tag-attached document.

The document creation system includes the write time/person additional write means and thus additionally writes the time at which the information has been written and a person who has written the information.

The document creation system includes the higher-level input item tag setting means and thus sets a higher-level input item tag in which multiple input item tags are organized, so that the input item tags can be referred to or written on the higher-level input item tag basis.

DETAILED DESCRIPTION

The present application is a system that is run using a computer.

This computer includes an input device (mouse, keyboard, etc.), an output device (monitor, printer, etc.), a storage device (memory, hard disk), a computing device (CPU), a controller (CPU), and the like, as well as includes a program for performing the means (functions) of the present application.

The document creation system includes the server apparatus, the database and the terminal. The server apparatus, the database and the terminal connected through network. The server apparatus is a prior computer. The server apparatus includes: an arithmetic apparatus including the processor, a main storage apparatus, an auxiliary storage apparatus, input apparatus, output apparatus, and communication apparatus. The arithmetic apparatus, the main storage apparatus, the auxiliary storage apparatus, input apparatus, output apparatus, the communication apparatus connected through a bus interface. The arithmetic apparatus includes the processor that can execute an instruction set. The main storage apparatus includes a volatile memory such as a random access memory (RAM). The auxiliary storage apparatus includes a recording medium such as a nonvolatile memory, and a recording method thereof is not limited. The recording medium indicates a hard disk drive (HDD) or a solid state drive (SSD), for example. The input apparatus is, for example, a keyboard device. The output apparatus includes, for example, display as a liquid crystal panel. The communication apparatus is a network interface that can connect to network. The processor of the server apparatus executes the function of the units of the document creation system including: an input item tag creation means, an input item tag list management means, a tag-attached document creation means or the like. The database is composed of the auxiliary storage apparatus of the server apparatus or the auxiliary storage apparatus independent from the server apparatus. The database stores information managed by the document creation system. The terminal is a prior computer including a processor.

Figure 1:
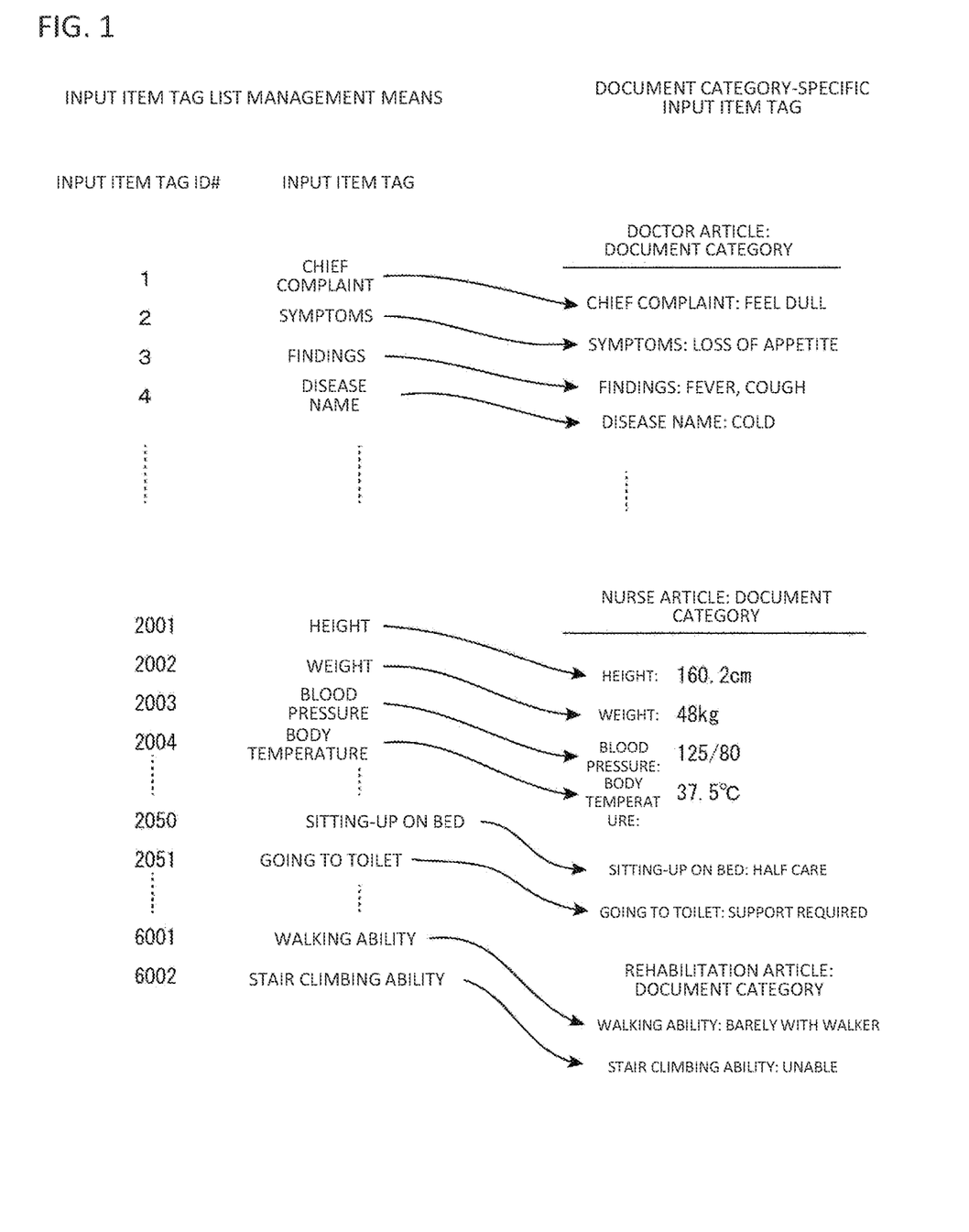
FIG. 1 is a diagram showing the relationships between a list of input item tags managed in input item tag list management means and input item tags placed in documents falling into different document categories.

FIG. 1 is a diagram showing the relationships between a list of input item tags managed in input item tag list management means and input item tags placed in documents (tag-attached documents) falling into different document categories.

In the input item tag list management means, input item tags (input item tag creation means) created and registered by a user are centrally managed using input item tag ID#.

Required input item tags are placed for each document category, and corresponding articles are inputted subsequent to ":" following the input item tags (tag-attached document creation means).

While a delimiter ":" is basically optionally placed between an input item tag and an input article, this is a desirable form because "input item tag:input article" takes a standard format called JSON as it is when recording document data.

Note that instead of JSON, an XML format such as <input item tag>input article</input item tag> may be used as a recording format in the computer.

Figure 2:
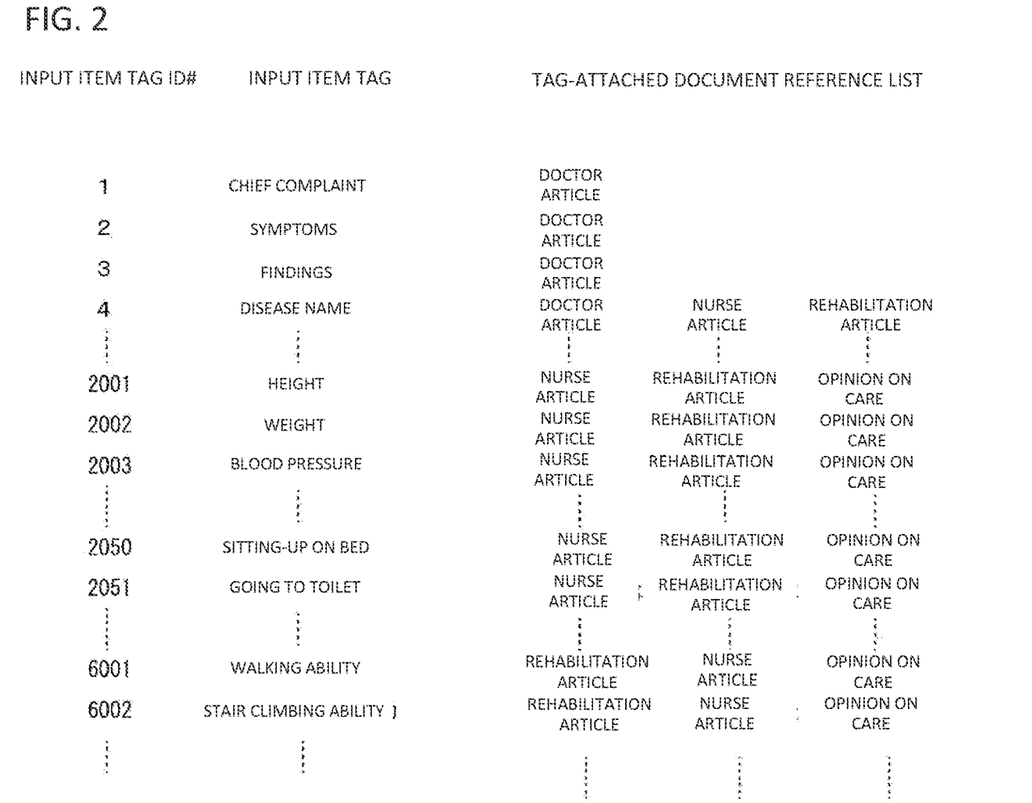
FIG. 2 is a diagram showing tag-attached document reference list management means.

FIG. 2 is a diagram showing tag-attached document reference list management means.

The tag-attached document reference list management means is recording, as tag-attached document reference lists, lists of document categories in which each input item tag is placed.

In FIG. 2, the first column of each document reference list is defined as a main tag-attached document category.

The second and later columns are defined as sub-tag-attached document categories. Information inputted to the input item tag in the main tag-attached document category is referred to or copied by the input item tag reference means (to be discussed later).

Note that the main or sub-tag-attached document category may be specified using another means.

If any information has yet to be inputted to the input item tag in the main tag-attached document category, a user may input information to the input item tag in any sub-tag-attached document category and then write the inputted information to the input item tag of the main tag-attached document category using input item tag write means (to be discussed later).

Figure 3:
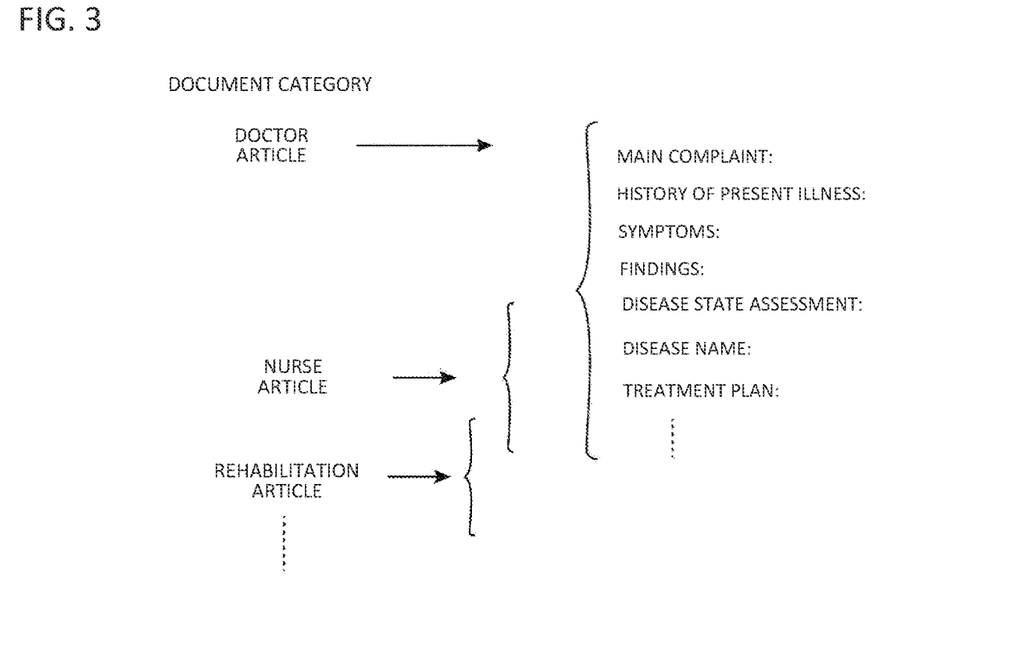
FIG. 3 is a diagram showing document category-specific model document management means.

FIG. 3 is a diagram showing document category-specific model document management means.

By previously creating input item tags to be placed, as models for each document category, the input item tags previously created as models are automatically placed when creating a document falling into the document category.

While FIG. 3 shows a doctor article as an example, models are also created for a nurse article, a rehabilitation article, and the like.

In some cases, it is useful to previously define, for example, as models in the document category "doctor article," multiple models for gastroenterologists, neurosurgeons, and the like and to selectively use those as necessary.

Figure 4:
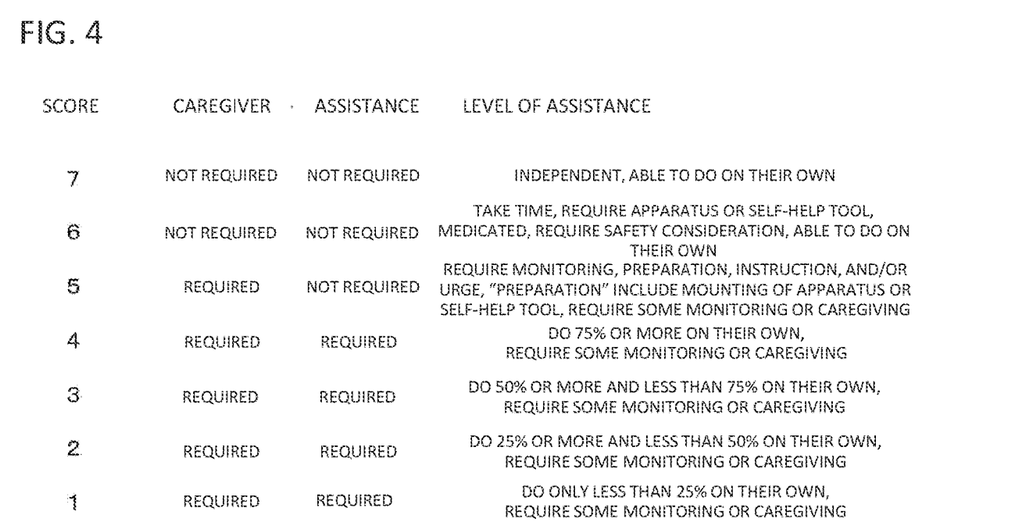
FIG. 4 is a diagram showing objectization of an input item tag.

FIG. 4 is a diagram showing objectization of an input item tag.

Rehabilitation ability such as "walking ability" is evaluated in accordance with evaluation criteria called FIM, and 1 to 7 is inputted as the evaluation result.

If text is freely inputted, the character expression such as halfwidth or fullwidth characters or "modified independence" fluctuates, resulting in a major obstacle to later statistical analysis.

For this reason, when this input item tag is inputted, a list as shown in FIG. 4 is shown so that an appropriate evaluation value can be selected. Thus, a correct, non-fluctuating description is easily made.

Such a list, options, the range of values to be inputted, or the like can be incorporated into an objectized input item tag.

By objectizing the input item tags and dragging and dropping the objectized input item tags from the input item tag list management means to a document category, a model document category can be easily created.

Also, in the case of simple text "walking ability:", ":" is often be erased or changed to ";" by the record/input person. This problem is solved by objectizing the input item tag.

While a correct, non-fluctuating description is easily made by objecting input item tags, recording a document including the objects requires a great amount of recording capacity for recording information on options as shown in FIG. 4.

For this reason, input is made using the objectized input item tags when editing a document, and plain text in the form of "input item tag: result," for example, "walking ability: 3" is recorded after the edit is complete. This requires only a small amount of recording capacity.

When reediting the document, the input item tag objects are restored by searching the input item tag list management means.

Figure 5:
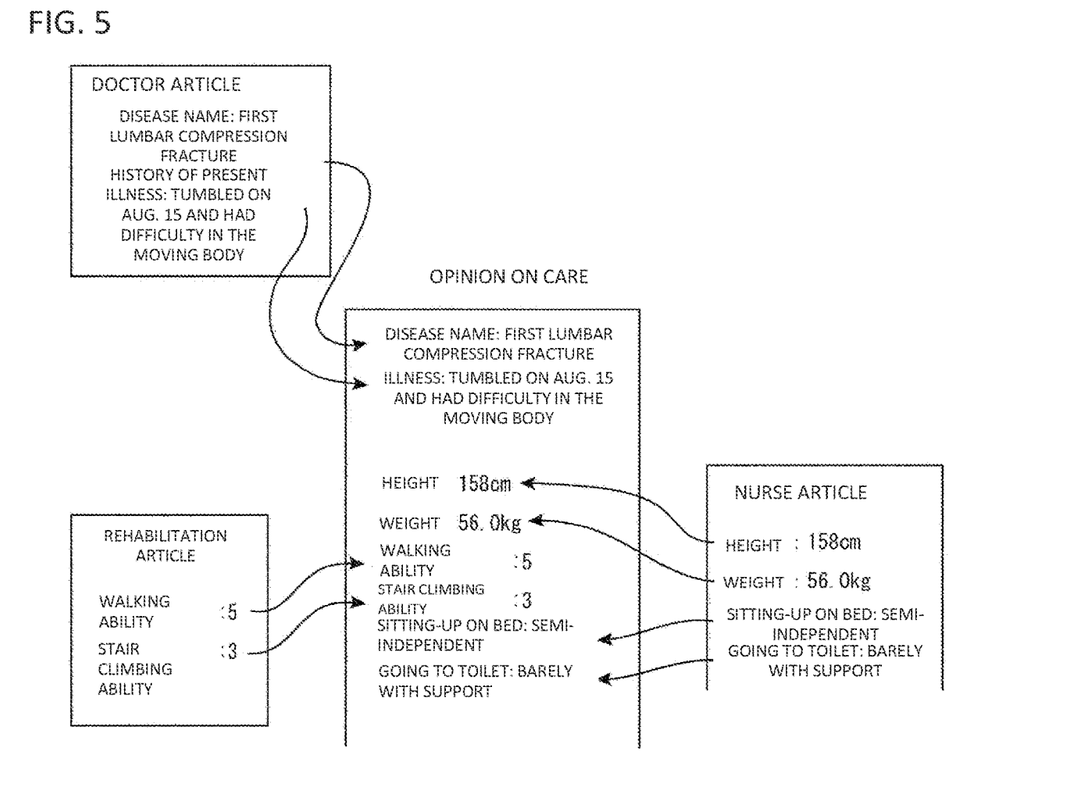
FIG. 5 is a diagram showing input item tag reference means.

FIG. 5 is a diagram showing input item tag reference means.

Most of information in an "opinion on care" is obtained by transcribing articles, such as a "doctor article," a "nurse article," and a "rehabilitation article."

Such transcription work has been done manually. On the other hand, in the present invention, the input item tags to be inputted or referred to are previously set as models in the main and sub-tag-attached document categories. Thus, at the same time when newly creating an "opinion on care" using the input item tags, articles of the corresponding input item tags in the main tag-attached document category are automatically referred to and transcribed to the input item tags in the "opinion on care".

Since the transcription work is automated, efforts for creating documents are significantly reduced. Also, if the input item tags previously placed as models but also other input item tags requiring reference are used when creating a document, the other input item tags may be dragged and dropped from the input item tag list management means. Thus, articles of the corresponding other input item tags in the main tag-attached document category are automatically referred to and transcribed to the other input item tags in the created document.

In some cases, it is necessary to grasp the situation of a patient or the like at a certain time point in the past. Such cases include a case in which it is necessary to report the monthly transition of movement ability from the time point of the patient's first visit in response to a question about the medical fee from an insurance company.

"Document articles," "nurse articles," and the like are recorded on a time-series basis, and grasping the situation at a certain time point across the articles often involves some difficulty.

In the present invention, when referring to required input item tags using the input item tag reference means, the time point is set using latest time point setting means. This allows the user to grasp the situation at each time point across the articles.

Figure 6A:
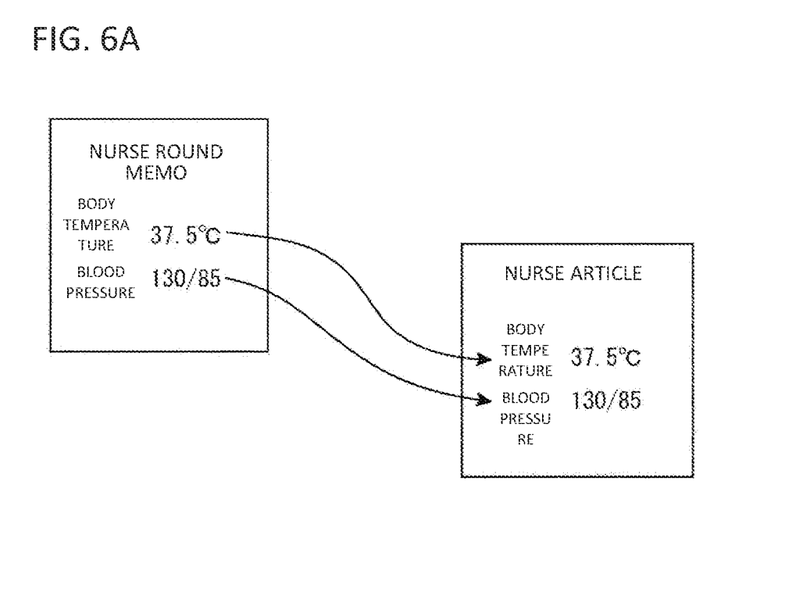
FIG. 6A is a diagram showing input item tag write means.

FIG. 6A is a diagram showing the input item tag write means.

While nurses measure the body temperature, blood pressure, and the like while making the rounds of hospital rooms, it takes time and effort to open a "nurse article" and input such data thereto each time. For this reason, it is efficient to write the measured blood pressure or body temperature to a "nursing round memo" such that the blood pressure or the like is transcribed to the corresponding input item tag in a "nurse article."

Figure 6B:
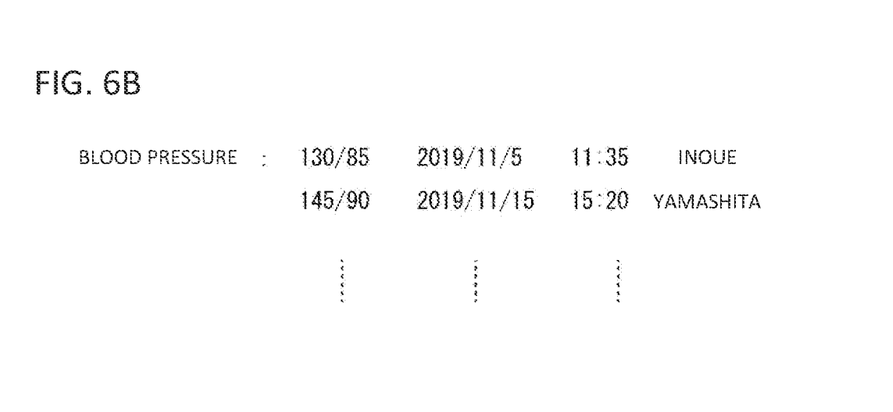
FIG. 6B is a diagram showing input item tag write means.

Since the creator of the "nurse article" and the creator of the "nursing round memo" are not necessarily the same, additionally writing the creation date/time and creator of the "nursing round memo" as shown in FIG. 6B is useful in clarifying where the responsibility of the record lies.

In some cases, it is necessary to make multiple measurements within the working hours. In such cases, as shown in FIG. 6B, the creation date/time and creator are additionally written each time a measurement is made (write time/person additional write means).

Figure 7:
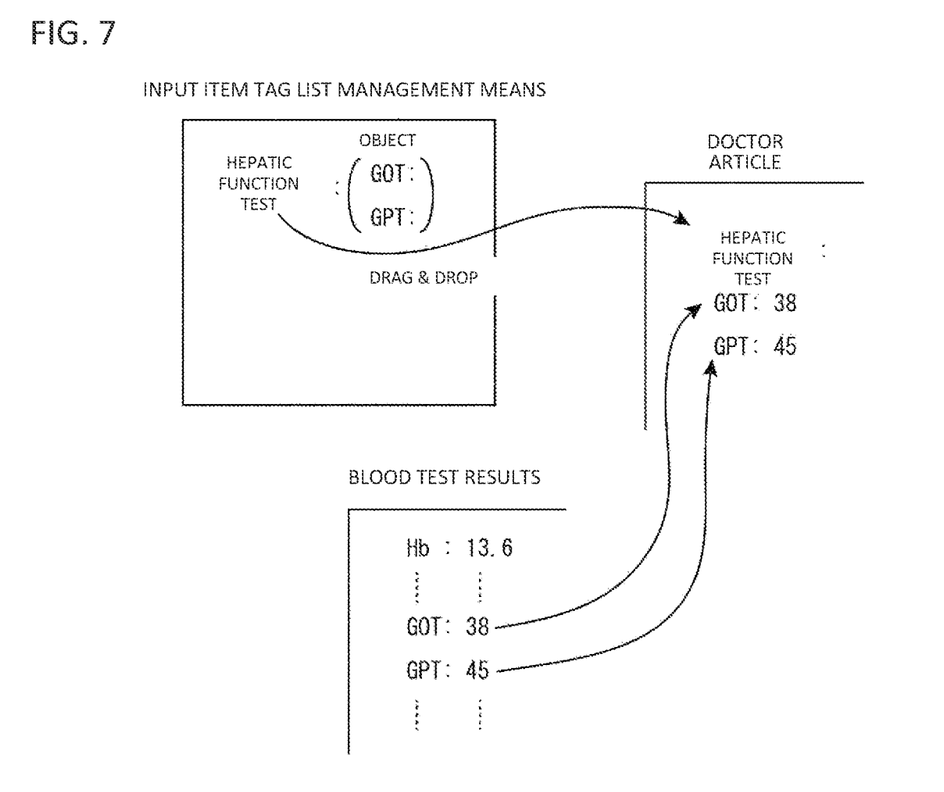
FIG. 7 is a diagram showing higher-level input item tag setting means.

FIG. 7 is a diagram showing higher-level input item tag setting means.

In FIG. 7, "hepatic function test:" registered in the input item tag list management means is used as an example higher-level input item tag.

Lower-level input item tags "GOT:", "GPT:", and the like are previously included in the attribute object of the higher-level input item tag "hepatic function test:". Thus, by dragging and dropping the higher-level input item tag, the lower-level input item tags are also dragged and dropped.

Thus, test data in the corresponding input item tags in a document "blood test results" is referred to instantly.

While an embodiment of the present invention has been described, the specific configuration of the present invention is not limited to the embodiment. Design changes and the like in the embodiment are included in the present invention without departing from the spirit and scope of the invention.

For example, while the present invention has been described using medical care as an example, the present invention is generally applicable to cases in which it is necessary to create and manage documents corresponding to each case and falling into multiple document categories or cases in which staff members in multiple job categories create a wide variety of complicated record documents, such as case situation observation records, research/problem-solving plans, and evaluations with respect to the executed plans.

The invention claimed is:

1. A document creation system for creating documents corresponding to each case and falling into a plurality of document categories, comprising:
    a processor; and
    a storage device; wherein
    the processor is configured to create input item tags,
    the processor is configured to manage a list of the input item tags,
    the input item tags are objectized so as to include attributes and a range of contents to be inputted thereof,
    the processor is configured to create a newly-created tag-attached document using the objectized input item tags,
    the processor is configured to record only plain text among the objectized input item tags when the processor finishes creating the document and is configured to record the document in the storage device,
    the processor is configured to, when creating the newly-created tag-attached document using the objectized input item tags, search for an existing tag-attached document including input item tags identical to the input item tags in the newly-created tag-attached document, and is configured to write the latest information described in the newly created tag-attached document by a nurse regarding a measurement results of a patient's temperature or blood pressure to the input item tags in the existing tag-attached document after retrieving the existing tag-attached document, and
    the processor is configured to additionally write a date and time at which the newly created tag-attached document was created and a name of the nurse who created the newly created tag-attached document to written content of the newly-created tag-attached document.

2. The document creation system of claim 1, wherein the processor is configured to manage a list of tag-attached documents referred to from the input item tags when creating a tag-attached document using the input item tags.

3. The document creation system of claim 1, wherein the processor is configured to register and manage a tag-attached document as a model of a document category.

4. The document creation system of claim 1, wherein the processor is configured to, when creating a tag-attached document using the input item tags, search for an existing tag-attached document including input item tags identical to the input item tags and to copy the latest information described in the input item tags in the retrieved existing tag-attached document to the input item tags in the created tag-attached document.

5. The document creation system of claim 4, wherein the processor is configured to set a time point in the past and to copy the latest information at the time point to the input item tags in the created tag-attached document.

6. The document creation system of claim 1, wherein the processor is configured to set a higher-level input item tag in which a plurality of input item tags are organized, so that the input item tags can be referred to or written on the higher-level input item tag basis.

* * * * *